(12) United States Patent
Wilen

(10) Patent No.: US 8,186,382 B2
(45) Date of Patent: May 29, 2012

(54) ROTATION VALVE FOR SAMPLE INJECTION

(75) Inventor: Anders Wilen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 512 days.

(21) Appl. No.: 12/523,356

(22) PCT Filed: Feb. 11, 2008

(86) PCT No.: PCT/SE2008/000111
§ 371 (c)(1),
(2), (4) Date: Jul. 16, 2009

(87) PCT Pub. No.: WO2008/103098
PCT Pub. Date: Aug. 28, 2008

(65) Prior Publication Data
US 2010/0032604 A1    Feb. 11, 2010

(30) Foreign Application Priority Data
Feb. 22, 2007    (SE) .................................... 0700462

(51) Int. Cl.
*F16K 11/074* (2006.01)
*G01N 30/20* (2006.01)

(52) U.S. Cl. .................................. 137/625.46; 73/61.55
(58) Field of Classification Search ............. 137/625.46; 73/61.55
See application file for complete search history.

(56) References Cited

U.S. PATENT DOCUMENTS

| | | | |
|---|---|---|---|
| 3,477,207 A | 11/1969 | Auger | |
| 3,868,970 A | 3/1975 | Ayers et al. | |
| 4,068,528 A | 1/1978 | Gundelfinger | |
| 4,158,630 A | 6/1979 | Stearns | |
| 4,552,178 A * | 11/1985 | Olsson | 137/625.46 |
| 4,625,569 A * | 12/1986 | Toei et al. | 73/863.72 |
| 5,010,921 A * | 4/1991 | Nohl | 137/625.46 |
| 5,623,965 A * | 4/1997 | Snider et al. | 137/596.2 |
| 6,012,488 A * | 1/2000 | Nichols | 137/625.11 |
| 6,155,123 A | 12/2000 | Bakalyar | |

* cited by examiner

*Primary Examiner* — John Fox

(57) ABSTRACT

A rotary valve adapted for injection of a fluid sample into a flow path. According to the invention one and the same valve can be used to input flow from a system pump, a sample pump and a syringe. A loop could be filled from both the sample pump and the syringe and the loop can be emptied by the system pump whereby for example a column is filled. Furthermore the sample pump can be used to pump directly to the column.

4 Claims, 7 Drawing Sheets

ROTATION VALVE FOR SAMPLE INJECTION

CROSS-REFERENCE TO RELATED APPLICATIONS

This application is a filing under 35 U.S.C. §371 and claims priority to international patent application number PCT/SE2008/000111 filed Feb. 11, 2008, published on Aug. 28, 2008, as WO 2008/103098, which claims priority to patent application number 0700462-5 filed in Sweden on Feb. 22, 2007.

FIELD OF THE INVENTION

The present invention relates to valves and more specifically to rotary valves used to introduce a sample into the flow path of an analytical or preparative instrument, such as a liquid chromatography system (LCS).

BACKGROUND OF THE INVENTION

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotator with respect to the stator.

Rotary valves can be designed to withstand high pressures (such as pressures above 30 MPa). They can be made from a range of materials, such as stainless steel, high performance polymeric materials and ceramics.

The number of inlets/outlets as well as the design of grooves in the rotor or the stator reflects the intended use of a specific valve.

A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

More complicated arrangements, tailor-made to perform one or several specific tasks, are possible. For instance, rotary valves may be used to introduce a fluid sample into the fluid path of an analytical system.

A typical example of such a valve is the INV-907 valve available from GE Healthcare. A schematic illustration of this valve is provided in FIG. 1 to 3. The valve 20 has a first inlet 1 for connection to a liquid source (such as a pump), a second inlet 2 for introduction of a sample (typically using a syringe or a dedicated sample pump), a third inlet 3 and a first outlet 4 to/from a device for temporary storage of the fluid sample such as a retaining capillary loop 22 (well known within the art), and a second outlet 5 that connects the valve to the downstream part of the analytical or preparative system e.g. an ÄKTA™ explorer system available from GE Healthcare. In addition, the valve has two waste outlets 6, 7 to allow a fluid to exit the valve directly to waste.

The orifices of the inner stator face of the INV-907 are represented by circles in FIG. 1-3, such as the circle 23 in the FIG. 2. In addition, a groove 24 is provided in the inner stator face.

In the figures, the rotor is represented by its grooves 25, 26, 27. When the rotor is rotated, the grooves change positions with respect to the inner stator face, thus enabling new flow paths through the valve.

FIG. 1 shows a "load position", wherein a sample may be introduced via the rotor groove 25 into the capillary loop 22 for temporary storage. At the same time the pump can provide a flow through the remaining system via the rotor groove 27. In this position, the stator groove 24 forms a small cul-de-sac.

FIG. 2 shows an "inject position", wherein the valve is now rotated 45° to allow the capillary loop 22 to form a part of the overall flow path of the system. The pump forces, via stator groove 24 and rotor grooves 27 and 25, the sample out of the capillary loop into the system for any separation, detection or other feature provided by the system. In this position, a part of the groove 27 forms a small cul-de-sac.

FIG. 3 shows a "waste position", allowing the pump to direct fluid directly to a waste outlet via rotor groove 27.

As mentioned above, the sample may be introduced either with a syringe or a dedicated sample pump. Using a conventional injection valve, for example of the type shown, requires that the sample pump is connected to the port that alternatively should be used for the syringe, i.e. both alternatives could not be used at the same time.

Therefore the user has to re-plumb the system to alternate between these operative modes which reduce the flexibility of the system.

SUMMARY OF THE INVENTION

An object of the invention is to provide a sample injection valve that is more flexible for the user.

This is achieved in a rotary valve according to claim 1 of the present application.

Hereby a sample injection valve is achieved which allows sample to be applied both by hand (for instance using a syringe) or automatically (such as by using a dedicated sample pump).

DETAILED DESCRIPTION OF THE INVENTION

Figure 1:
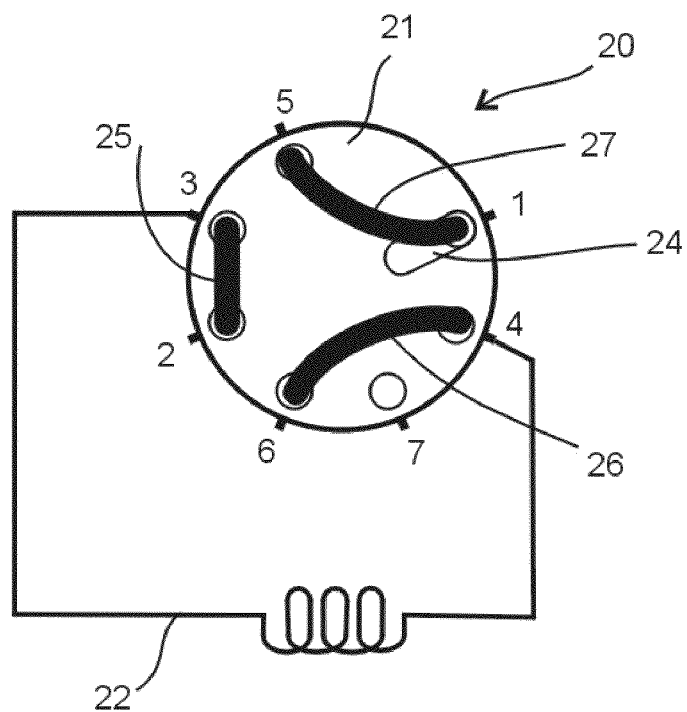
FIG. 1 is a schematic view of a prior art introduction valve in a load position.
Figure 2:
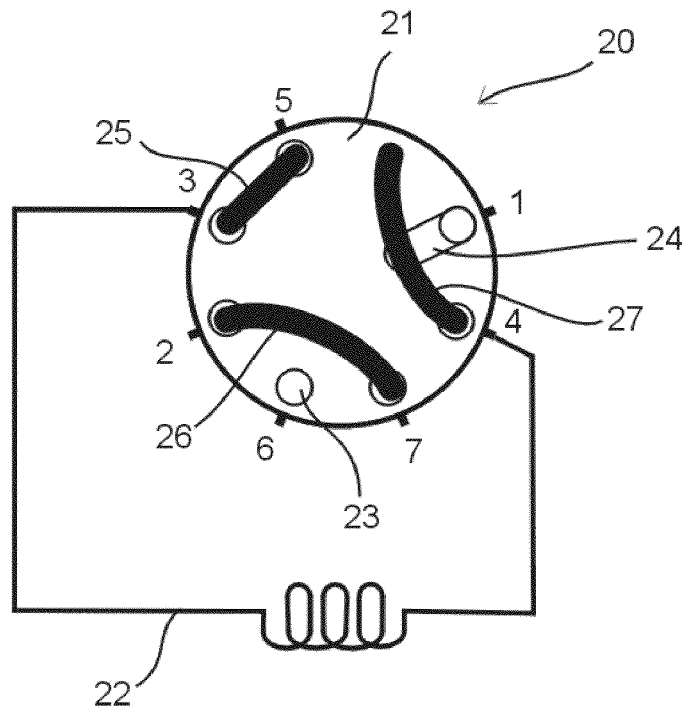
FIG. 2 shows the valve of FIG. 1 in an inject position.
Figure 3:
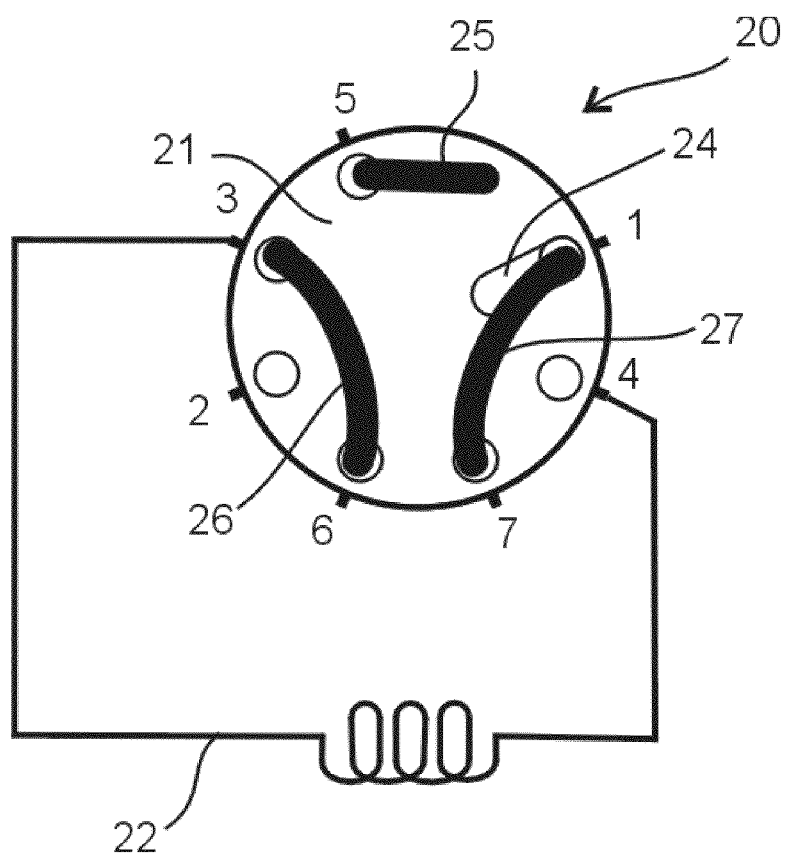
FIG. 3 shows the valve of FIG. 1 in a waste position.
Figure 4:
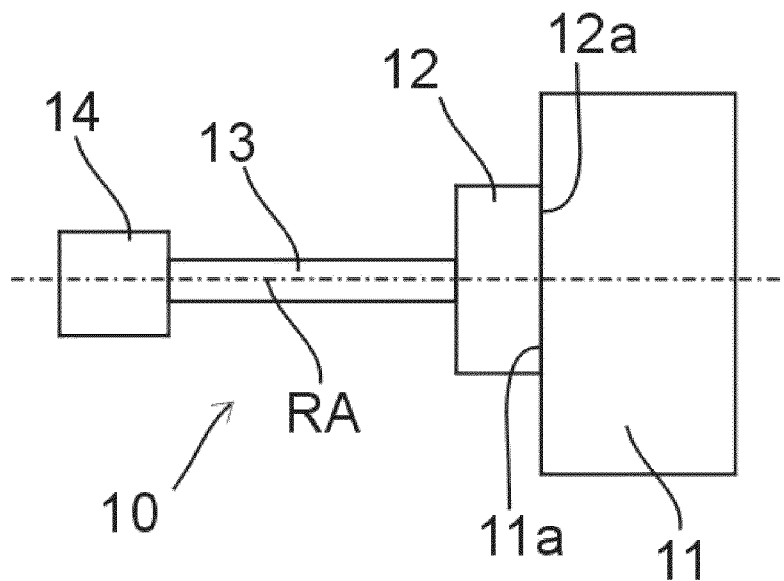
FIG. 4 is a schematic side view of a rotary valve.

The main parts of a typical rotary valve 10 are schematically shown in FIG. 4 (wherein no brackets or similar load carrying or fastening elements are shown). The rotary valve 10 has a stator 11, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 11, which is fixed with respect to the instrument into which it is built, is provided with ports (not shown in FIG. 4) for fluid communication with a fluid source and any components with which the valve is to co-operate. The ports may be positioned on any suitable position on the exterior surface of the stator. The ports are provided with means to connect capillaries or tubing. Such means may be of any suitable type, such as conventional Valco fittings well known to anyone skilled in the art. The ports are via channels in fluid communication with a corresponding set of orifices on an inner stator face 11a, i.e. that surface of the stator 11 that during operation is in contact with the rotor 12.

The rotor 12 is typically formed as a disc and has an inner rotor face 12a that is that face that is pressed against the inner stator face 11a during operation. The inner rotor face 12a is provided with one or more grooves which interconnect different orifices of the inner stator face 11a depending on the rotary position of the rotor 12 with respect to the stator 11.

Figure 5:
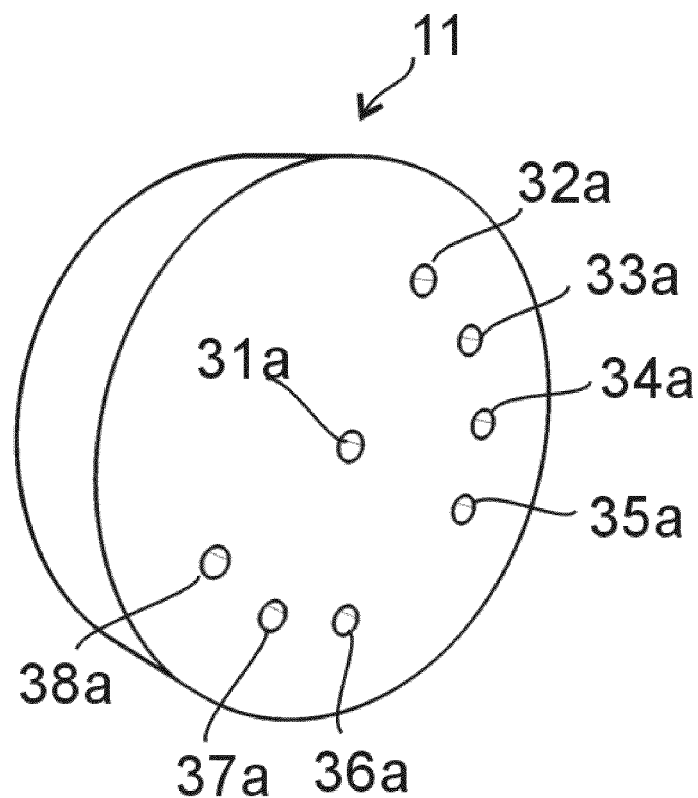
FIG. 5 shows the front side of a valve stator according to one embodiment of the invention.

FIG. 5 shows a simplified perspective view of the front side of a stator 11 according to one embodiment of the invention. The front side is here the side of the stator 11 opposite the inner stator face 11a. Inlet and outlet ports 31a-38a are illustrated.

Generally, it should be noticed that the angular position of ports, grooves and similar shown in the figures of the present application could differ between different embodiments of the invention, i.e. they could be turned with respect to the rotary axis of the valve, mirrored or altered in other ways as long as their mutual co-operation is still according to the inventive idea.

In addition, since the inlet/outlet ports in the stator are connected to orifices on the inner stator face 11a via bores (or any type of channels) it is possible to arrange the ports in a way that differs from the pattern of orifices on the inner stator face 11a by making non-linear channels between the ports and the orifices. The ports into the stator can even be positioned on another outer surface of the stator than the front side. However, for reasons of simplicity, the ports are shown as being positioned in-line with the inner stator face orifices as will be described below in relation to FIG. 6.

Thus, the stator 11 according to one embodiment of the present invention has eight ports 31a-38a that are used to connect the valve to all desired operative components of the instrument. According to other embodiments of the invention one or more additional orifices and ports can be provided to give some additional features to the valve.

Port 31a is called a first inlet port 31a. It is positioned essentially in the middle of the stator and is used as inlet port from a main liquid source of the instrument, such as a pump, herein called the system pump. In the case of a Liquid Chromatography System, LCS, the system pump provides a flow of a single, so called buffer liquid or, alternatively, a fixed or variable mixture of two or more buffer liquids. Port 34a is called a first outlet port 34a and serves as the outlet port from which the liquid is allowed to exit to the remaining part of the instrument.

A retaining loop, such as a conventional capillary loop for use in a LCS, is in this embodiment connected at one end to a first connection port 32a and at the other end to a second connection port 35a.

Two ports 36a, 37a, here called second and third inlet ports 36a, 37b are provided for introduction of a sample. In the preferred embodiment shown, the third inlet port 37a is intended for manual sample injection, typically using a syringe, while the second inlet port 36a is intended to be connected to a dedicated sample pump. The sample pump may be integrated in the instrument, or it may be a stand-alone device.

The ports 33a and 38a are called second and third outlet ports 33a and 38a and are in this embodiment waste outlet ports.

Figure 6:
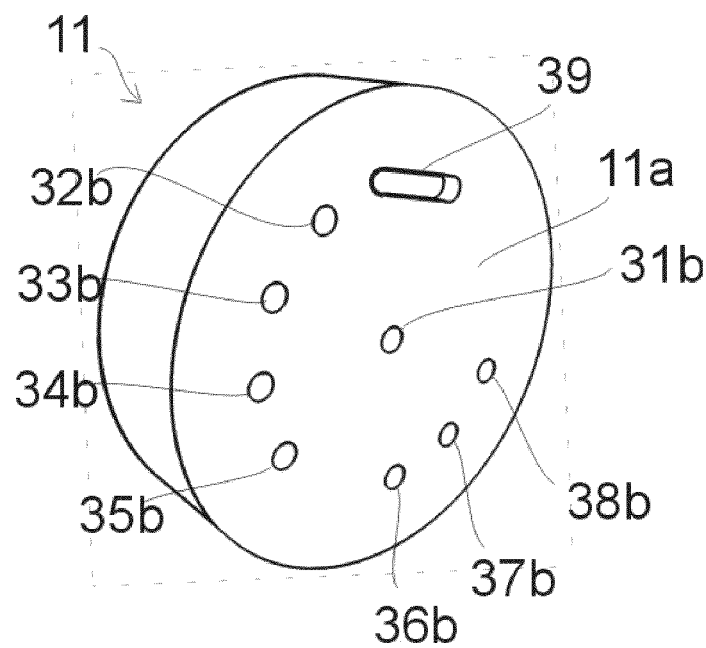
FIG. 6 shows the inner stator face of the stator of FIG. 5.

FIG. 6 is a perspective view of the stator 11 of FIG. 5 viewed from the other side, i.e. the inner stator face side 11a. Note that each port is connected to the inner stator face 11a via a channel ending in an orifice 32b-38b shown in the figure. For reason of simplicity, the orifice with number 32b is connected to the port with number 32a and so on.

In addition to the orifices connected to the ports, a stator groove 39 is in this illustrated embodiment provided in the inner stator face 11a. The stator groove 39 is typically of the same width as an orifice diameter. It should be noted that although the stator groove 39 is preferred in order to allow the system pump to pump liquid through the system while the sample pump fills the loop (this will be described in detail below), it is not essential for the inventive idea. Without the stator groove 39 the system pump must either be at still when the sample pump fills the loop or there should be an additional waste outlet provided in the stator. For example another waste outlet may be provided between the second connection orifice 35b and the second inlet orifice 36b.

Figure 7:
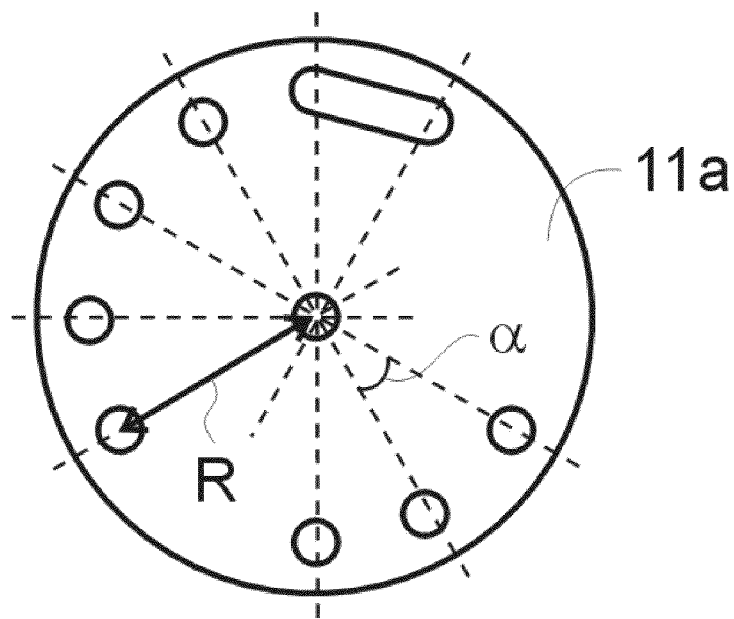
FIG. 7 shows the angular distribution of the orifices in the inner stator face according to one embodiment of the invention.

Looking at the inner stator face 11a, the general angular distribution of the orifices and the ends of the groove 39 for one embodiment of the invention is illustrated in FIG. 7. The positions for orifices, groove ends (and not used positions) are here shown to be equally distributed around the center of the stator (which center coincides with the rotary axis of the valve). As described above the positions of the orifices can be varied slightly without departing from the inventive idea. Since there are 12 such positions on the stator according to this embodiment, the partition angle α is 30° in this embodiment. All these positions are placed with essentially the same radial distance R to the rotational axis of the valve.

Figure 8:
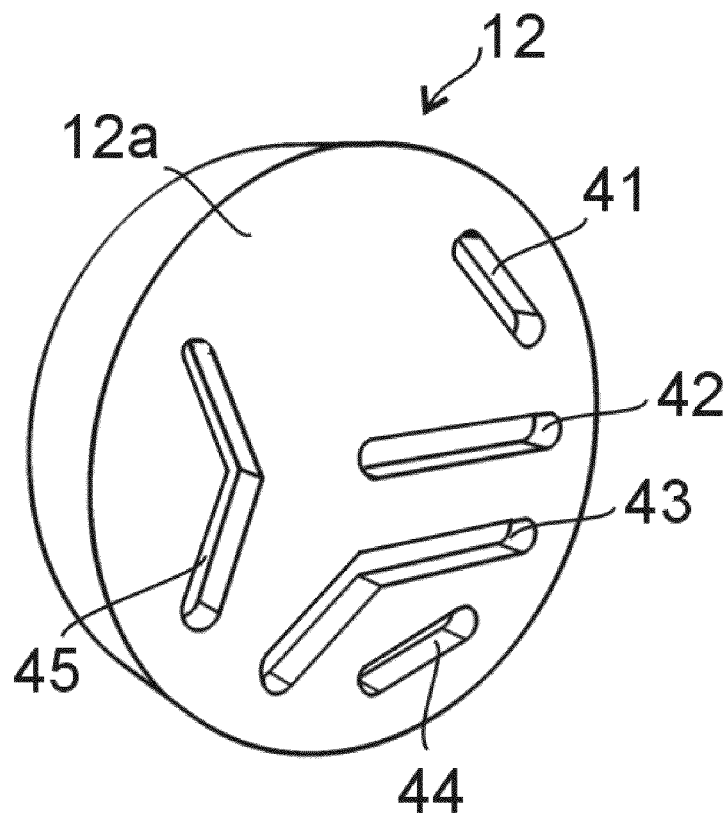
FIG. 8 shows the inner rotor face of a rotor according to one embodiment of the invention.
Figure 9:
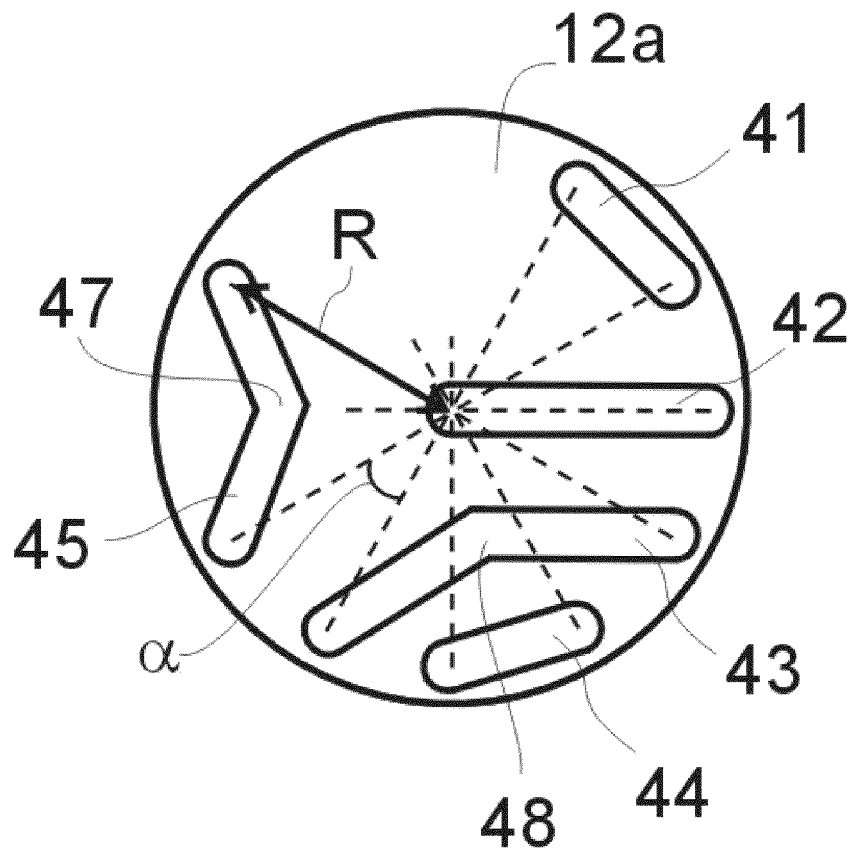
FIG. 9 shows the positions of the grooves in the inner rotor face according to one embodiment of the invention.

The inner rotor face 12a of the rotor 12 of a valve embodiment according to the present invention is shown in FIG. 8. It is provided with five grooves, called the first, second, third, fourth and fifth groove 41-45. The mutual positions and shapes of the grooves are more clearly illustrated in FIG. 9.

Each groove has both its ends ending at essentially the same radial distance R from the center, except for one end of groove 42 that ends in the center of the inner rotor face 12a (coinciding with the rotary axis of the valve). Of course, the radial distance R for the rotor is the same as the corresponding radial distance R of the stator. The first groove 41 extends over an angle α, which in the present embodiment is 30°. The second groove 42 is a straight groove from the center of the inner rotor face 12a out towards the rim, with a length of R, and is parted from the nearest end of the first groove 41 by the angle α. The third groove 43 begins at a position parted by the angle α from second groove 42, and ends at a position that is separated from the start position by an angle of 3 α. It is bent inwards toward the centre to form a knee 48 (or alternatively in an arcuate shape). The fourth groove 44, which occupies angle α, is equidistantly placed between the ends of groove 43. The fifth groove 45 has a shape similar to that of the third groove 43 (with a knee 47 displaced inwardly towards the center) but the end points are parted by an angle of 2 α, and begins at an angle α from the closest end of the third groove 43.

When assembled, the inner rotor face 12a is pressed against the inner stator face 11a in a manner that is typical for any conventional rotary valve (which is well known for anyone skilled in the art, and will not be explained herein). Depending on the mutual angular positions of the rotor 12 and the stator 11 different operation modes are obtained for the valve. These are illustrated in FIG. 10-13, wherein the grooves of the rotor are indicated by thick lines.

Figure 10:
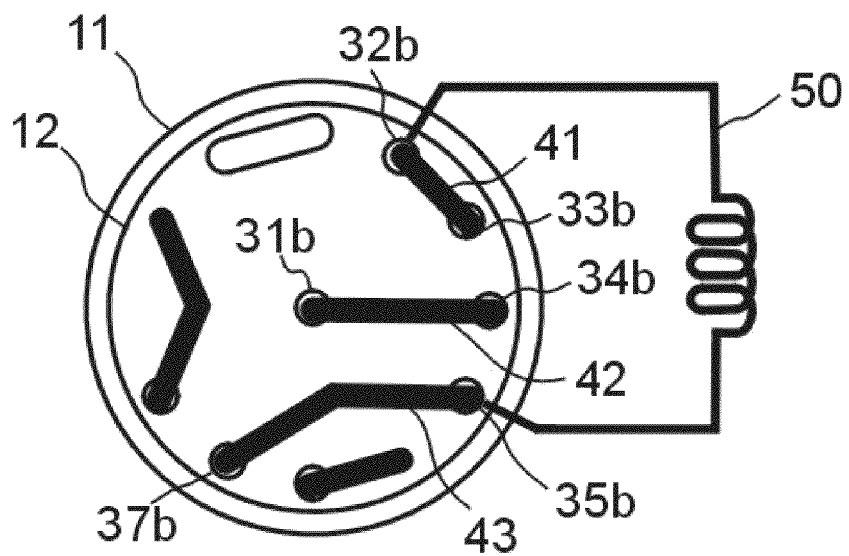
FIG. 10 is a schematic view of a first rotor position.

In the first rotor position, as shown in FIG. 10, the valve allows two separate flow paths.

Fluid entering the first inlet orifice 31b, typically from a pump, such as a system pump of a LCS, and of course through the first inlet port 31a, is allowed to pass through the valve via the second groove 42 and out of the first outlet orifice 34b and further out through the first outlet port 34a. In the case of a LCS, the first outlet port 34a is intended to be connected to the main operative components of the instrument such as a chromatography column and monitoring devices such as UV monitors. In FIGS. 10-13 grooves and orifices are shown and referred to and it is understood that each of said orifice mentioned is connected to a corresponding port as described above.

At the same time it is possible to temporarily store a sample in a capillary loop 50 (or any device with a corresponding function) by introducing it through the third inlet port 37a. This is typically done with a syringe. After entering the third inlet port 37a and further through the third inlet orifice 37b, the sample passes the third groove 43 to enter the loop 50 via the second connection orifice and port 35b and 35a. The loop 50 is connected to the second connection port 35a and at its other end to the first connection port 32a. Hereby fluid in the loop is allowed to exit to waste via the first groove 41 and the second outlet orifice and port 33b and 33a.

The other orifices, ports and grooves of the valve are not active in the first rotor position.

Figure 11:
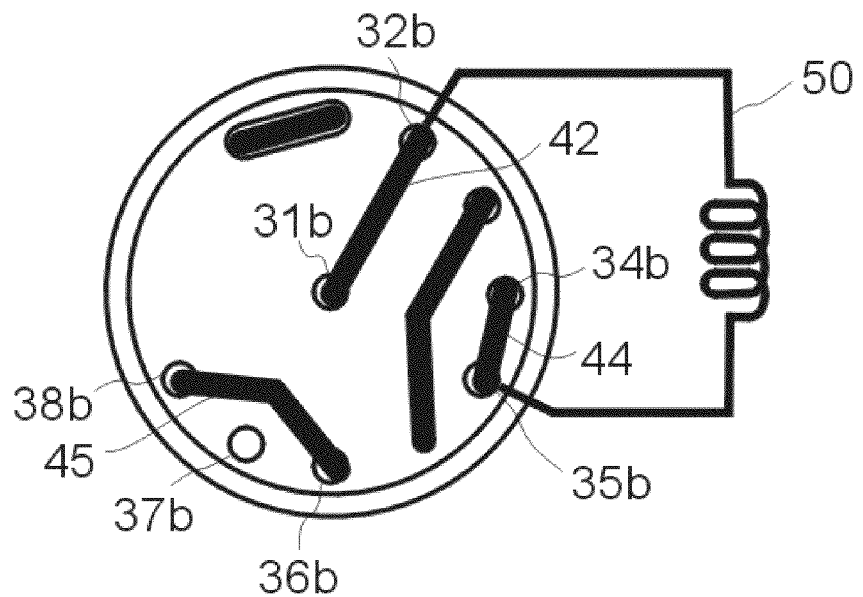
FIG. 11 is a schematic view of a second rotor position.

The second rotor position, as shown in FIG. 11, is obtained by rotating the rotor an angle of 2×α counterclockwise (as seen from the view of FIG. 10) with respect to the first rotor position and allows two separate flow paths.

The fluid that enters through the first inlet port orifice 31a, 31b will now pass through the valve via the second groove 42 and into the loop 50 via the first connection orifice and port 32b,a. Thus, the content of the loop will be forced into the main operative components of the instrument via the second connection port and orifice 35a, 35b, the fourth groove 44 and the first outlet orifice and port 34b,a. It should be noted that the sample is expelled using an opposite flow direction through the loop 50 with respect to how it was loaded, thus allowing it to travel the shortest possible way which is beneficial since it reduces the sample dilution to a minimum.

At the same time a flow from a dedicated sample pump connected to the second inlet port 36a may be pumped to waste via the fifth groove 45 and the third outlet orifice and port 38b and 38a. This is useful for rinsing the tubing of the sample pump, as well as for rinsing the fifth groove 45.

The other ports and grooves of the valve are not active in the second rotor position.

Figure 12:
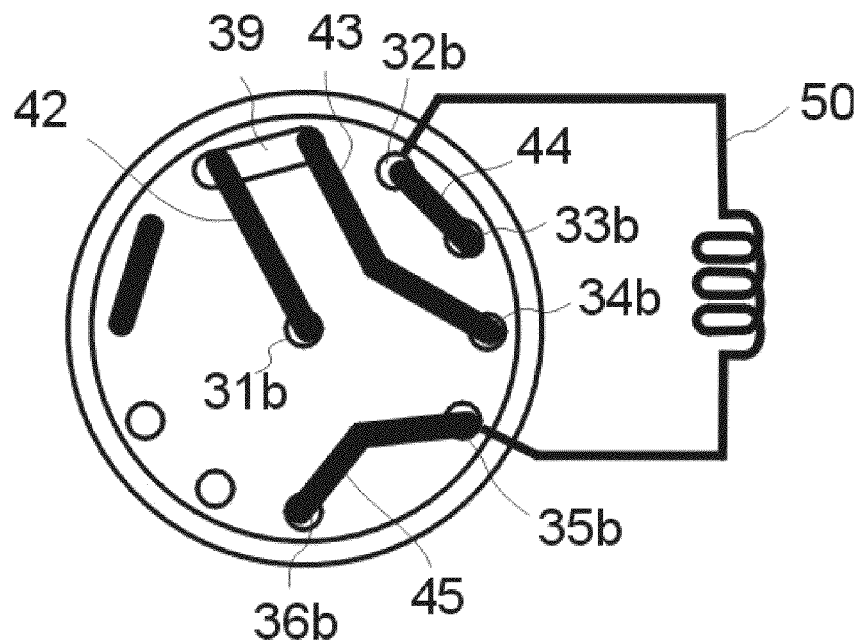
FIG. 12 is a schematic view of a third rotor position.

The third rotor position, as shown in FIG. 12, is obtained by rotating the rotor an angle of 4×α counterclockwise (as seen from the view of FIG. 10) with respect to the first rotor position. As for the first and the second position, the third rotor position allows two separate flow paths through the valve.

The fluid that enters through the first inlet port and orifice 31a and 31b will pass through the valve via the second rotor groove 42, the stator groove 39, the third rotor groove 43 and out of the valve via the first outlet orifice and port 34b and 34a into the main operative components of the instrument as described above. This allows these grooves to be rinsed at the same time as a flow can be provided to the main operative components of the instrument. However, as mentioned above, it is possible to replace the groove 39 with a waste outlet at the end position of the second groove 42, or even a dead-end. However, in these cases no flow will be available through the main operative components of the system.

At the same time it is possible to temporarily store a sample in the capillary loop 50 by introducing it through the second inlet port and orifice 36a and 36b. This is preferably done with a dedicated sample pump, as is well known in the art of liquid chromatography. After entering the second inlet orifice 36b the sample passes the fifth groove 45 to enter the loop 50 via the second connection orifice and port 35b and 35a. At its other end the loop 50 is connected to the first connection port 32a to allow fluid in the loop to exit to waste via the first connection orifice 32b, the fourth groove 44 and the second outlet orifice and port 33b and 33a.

The other ports, orifices and grooves of the valve are not active in the third rotor position.

Emptying of the loop 50 is performed using the second rotor position, as described above.

Figure 13:
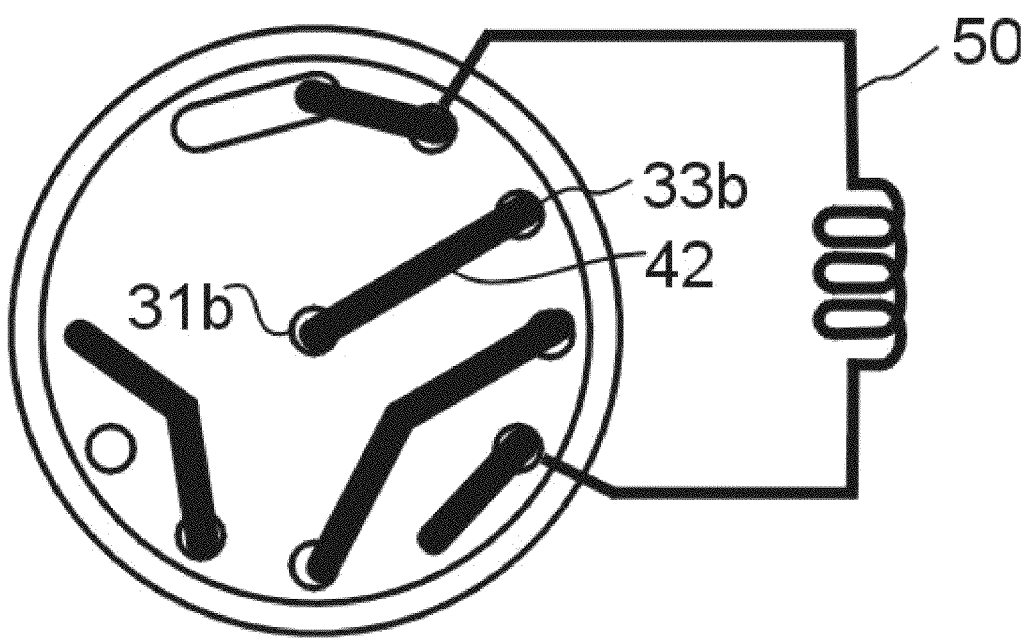
FIG. 13 is a schematic view of a fourth rotor position.

In this described embodiment also a fourth rotor position, as shown in FIG. 13, is useful, although not necessary for the inventive use of the valve. The fourth rotor position is obtained by rotating the rotor an angle α counterclockwise (as seen from the view of FIG. 10) with respect to the first rotor position.

In the fourth rotor position, the fluid that enters through the first inlet port and orifice 31a and 31b will pass directly to the waste outlet via the second rotor groove 42 and the second outlet orifice and port 33b and 33a. This position may be used in a case when it is desired to run the main pump of the instrument without forcing any fluid through the main operative components of the instrument downstream of the valve.

As described above the exact position of the orifices need not to be according to the embodiment described above. What is important for the invention is that the different grooves reaches the specific orifices that should be reached in each rotation position described above.

What is claimed is:

1. A rotary valve (10) adapted for injection of a fluid sample into a flow path, the valve comprising a stator (11) and a rotor (12), said stator (11) comprising a number of connection ports protruding into the stator and each ending in an orifice on an inner stator face (11a), which is a face of the stator making contact in a fluid tight manner with an inner rotor face (12a) of the rotor (12), said inner rotor face (12a) being rotatably movable around a rotational axis (RA) relative to the inner stator face (11a), wherein said inner stator face (11a) comprises:
  a first inlet orifice (31b) communicating with a first inlet port (31a) to the stator, said first inlet orifice (31b) being positioned essentially centrally in the inner stator face (11a), which center coincides essentially with the rotary axis (RA) of the valve, a second inlet orifice (36*b*) communicating with a second inlet port (36*a*) to the stator, a third inlet orifice (37*b*) communicating with a third inlet port (37*a*) to the stator, a first outlet orifice (34*b*) communicating with a first outlet port (34*a*) of the stator, a second outlet orifice (33*b*) communicating with a second outlet port (33*a*) of the stator, a third outlet orifice (38*b*) communicating with a third outlet port (38*a*) of the stator, a first connection orifice (32*b*) communicating with a first connection port (32*a*) of the stator, a second connection orifice (35*b*) communicating with a second connection port (35*a*) of the stator, and wherein said second and third inlet orifices (36*b*, 37*b*), said first, second and third outlet orifices (34*b*, 33*b*, 38*b*) and said first and second connection orifices (32*b*, 35*b*) are distributed substantially on a circle around the center of the inner stator face (11*a*), said circle having a radius (R), and further wherein:

said inner rotor face (12*a*) comprises a first groove (41), a second groove (42), a third groove (43), a fourth groove (44) and a fifth groove (45) so arranged that, in a first rotary position of the rotor:

the first groove (41) connects the first connection orifice (32*b*) with the second outlet orifice (33*b*), the second groove (42) connects the first inlet orifice (31*b*) with the first outlet orifice (34*b*), and the third groove (43) connects the second connection orifice (35*b*) with the third inlet orifice (37*b*), in a second rotary position of the rotor:

the second groove (42) connects the first inlet orifice (31*b*) with the first connection orifice (32*b*), the fourth groove (44) connects the first outlet orifice (34*b*) with the second connection orifice (35*b*), and the fifth groove (45) connects the second inlet orifice (36*b*) with the third outlet orifice (38*b*), in a third rotary position of the rotor:

the fourth groove (44) connects the second outlet orifice (33*b*) with the first connection orifice (32*b*), and the fifth groove (45) connects the second inlet orifice (36*b*) with the second connection orifice (35*b*).

2. The rotary valve of claim 1, wherein the stator further comprises a stator groove (39), said stator groove (39) having both its ends positioned substantially on the radial distance R from the center of the inner stator face and wherein the rotor grooves further are so arranged that in the third rotary position of the rotor:

the second groove (42) connects the first inlet orifice (31*b*) with the stator groove (39) and the third groove (43) connects the first outlet orifice (34*b*) with the stator groove (39).

3. The rotary valve of claim 2, wherein the rotor could be positioned in a fourth rotary position where the second groove (42) connects the first inlet orifice (31*b*) with the second outlet orifice (33*b*).

4. The rotary valve of claim 1, wherein the rotor could be positioned in a fourth rotary position where the second groove (42) connects the first inlet orifice (31*b*) with the second outlet orifice (33*b*).

* * * * *